United States Patent
Hansen

[19]

[11] Patent Number: 6,083,169

[45] Date of Patent: Jul. 4, 2000

[54] METHOD AND AN APPARATUS FOR THE INSERTION OF A NEEDLE GUIDE INTO A PATIENT IN ORDER TO REMOVE TISSUE SAMPLES

[75] Inventor: Niels Stengaard Hansen, Værløse, Denmark

[73] Assignee: B & K Ultrasound Systems A/S, Gentofte, Denmark

[21] Appl. No.: 08/945,214

[22] PCT Filed: Apr. 19, 1996

[86] PCT No.: PCT/DK96/00177

§ 371 Date: Oct. 10, 1997

§ 102(e) Date: Oct. 10, 1997

[87] PCT Pub. No.: WO96/32889

PCT Pub. Date: Oct. 24, 1996

[30] Foreign Application Priority Data

Apr. 19, 1995 [DK] Denmark ................................. 0453/95

[51] Int. Cl.[7] .......................................................... A61B 8/00
[52] U.S. Cl. .............................................................. 600/461
[58] Field of Search .................................... 600/461, 567, 600/439, 463

[56] References Cited

U.S. PATENT DOCUMENTS

| | | |
|---|---|---|
| 4,763,662 | 8/1988 | Yokoi . |
| 4,911,173 | 3/1990 | Terwilliger . |
| 5,256,149 | 10/1993 | Banik et al. . |
| 5,335,663 | 8/1994 | Oakley et al. . |
| 5,437,283 | 8/1995 | Ranalletta et al. . |

*Primary Examiner*—Marvin M. Lateef
*Assistant Examiner*—Maulin Patel
*Attorney, Agent, or Firm*—Pillsbury Madison & Sutro LLP

[57] ABSTRACT

An apparatus for the insertion of a needle guide in a patient so as to remove in an ultrasound guided manner intraoperative tissue samples (biopsies) includes a mounting member for the mounting of the needle guide on an ultrasonic transducer at the end of a catheter. The needle guide is predominantly flexible, but is rigid at the end at the mounting member. As a result, a needle inserted through the needle guide can be guided in the image plane of the ultrasonic transducer and displayed on a display unit associated with the ultrasonic transducer. The needle guide and the transducer can be operated through one and the same trocar, or each through their respective individual trocar.

8 Claims, 7 Drawing Sheets

METHOD AND AN APPARATUS FOR THE INSERTION OF A NEEDLE GUIDE INTO A PATIENT IN ORDER TO REMOVE TISSUE SAMPLES

This application is the national phase of international application PCT/DK96/00177 filed Apr. 19, 1996 which designated the U.S.

TECHNICAL FIELD

The invention relates to an apparatus for the insertion of a needle guide to be used for the ultrasound-guided removal of tissue samples (biopsies) and comprising a mounting member for the mounting of the needle guide on an ultrasound transducer.

BACKGROUND ART

Needle guide systems are known in connection with ultrasonic transducers for removal of samples from internal organs.

A first needle guide system is a rigid system mounted on the side of the transducer, and which ensures that the needle is inserted in the ultrasonic image plane and imaged on the display associated with the ultrasonic transducer. Such a system requires relatively much room and accordingly it can only be used in connection with open operations (laparotomy). Relatively short needles are used which may be rather thick.

The same principle may apply to an ultrasonic transducer where the needle is inserted together with the transducer through a trocar tube. In this manner, ultrasound guided biopsies can be performed through the trocar tube. The latter is referred to as laparoscopic ultrasound-guided biopsy. The advantage of such a procedure is that the operational wound is smaller than the wound resulting from the first system. However, like the first needle guide system, this system only allows removal of tissue samples in one direction, viz. in an outward direction from the insertion point. Such a procedure is not always sufficient, for instance in connection with removal of tissue samples from organs full of blood, such as a liver, where the shortest possible insertion of the needle into the tissue is desired.

Furthermore, a flexible needle guide system is known, which is used together with an endoscope with an ultrasonic transducer built thereon, cf. PENTAX ultrasound upper G. I. fibrescope type FG-320A. A needle placed in a spiral is inserted through the endoscope into a channel which ensures that once the needle has left the channel and been inserted into the tissue, it is moved into the image plane of the transducer and imaged on a display associated with the transducer. The endoscope is flexible and suited for insertion through the natural openings of the body, such as through the mouth and the gullet and down into the stomach. The flexibility of the endoscope renders it unsuited for removal of biopsies from internal organs in the abdominal cavity because the positioning and the retaining of the instrument in the desired position are only possible in tubular cavities, such as inside the gullet. A drawback of the latter transducer is that the measuring system must be very flexible in order to be suited for ultrasound-guided biopsies at a predetermined depth, because the needle must then be able to withstand a bending of a relatively small radius.

SUMMARY OF THE INVENTION

The object of the invention is to provide a needle guide without the above drawbacks, and which is more flexible than the previously known needle guides.

An apparatus of the above described type is according to the invention characterised in that the needle guide is predominantly flexible, but rigid at the end at the mounting member and can be inserted through a trocar, and that a needle inserted through the needle guide can be guided in the image plane by the ultrasonic transducer and imaged on a display associated with the ultrasonic transducer. The resulting needle guide is independent of the catheter, and the movements of the operator are more free than previously allowed.

BRIEF DESCRIPTION OF THE DRAWINGS

The invention is explained in greater detail below with reference to the accompanying drawings, in which.

DETAILED DESCRIPTION OF THE BEST MODE FOR CARRYING OUT THE INVENTION

Figure 1:
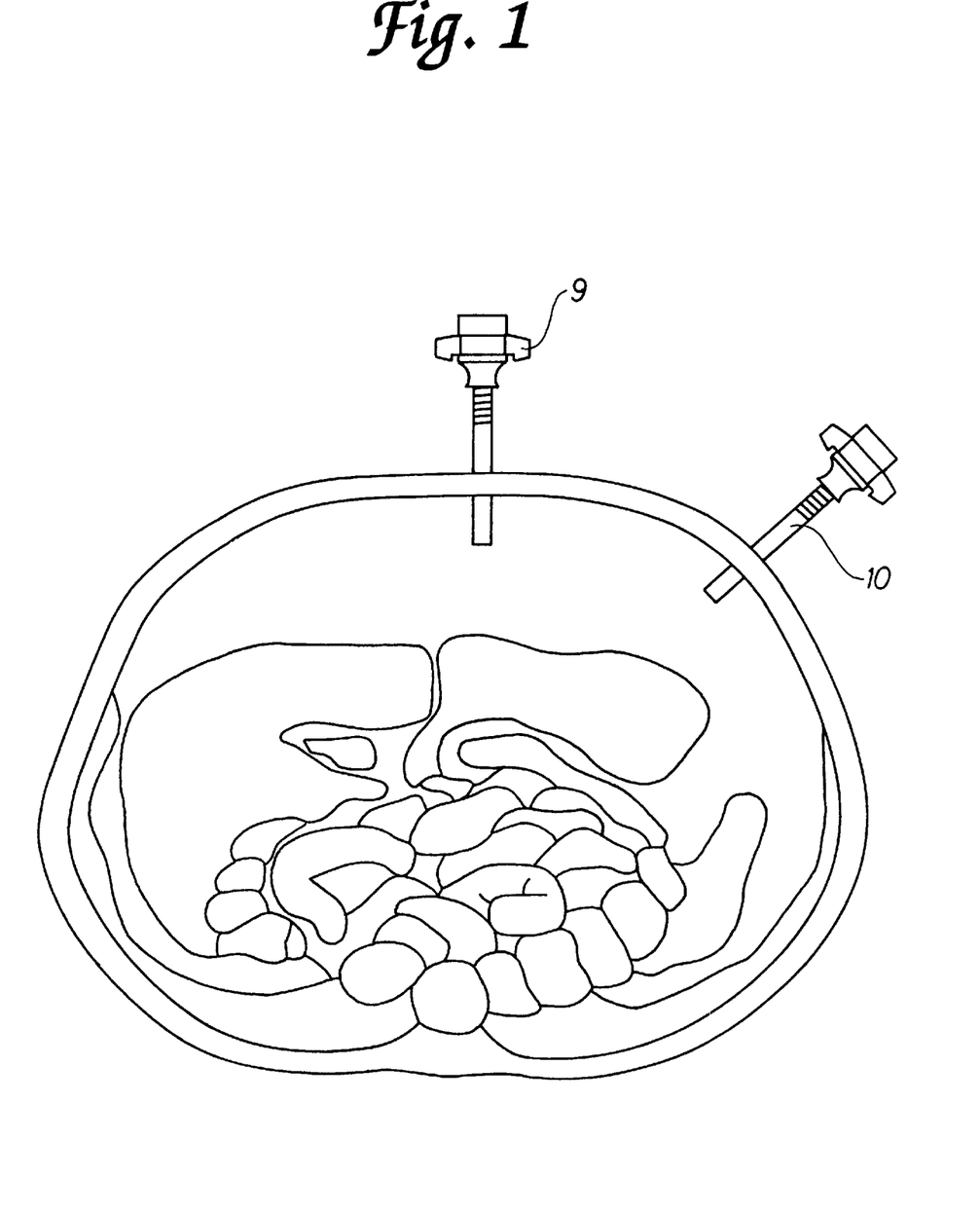
FIG. 1 illustrates some trocars inserted in a distended abdominal cavity of a patient.
Figures 2, 2A, 2B:
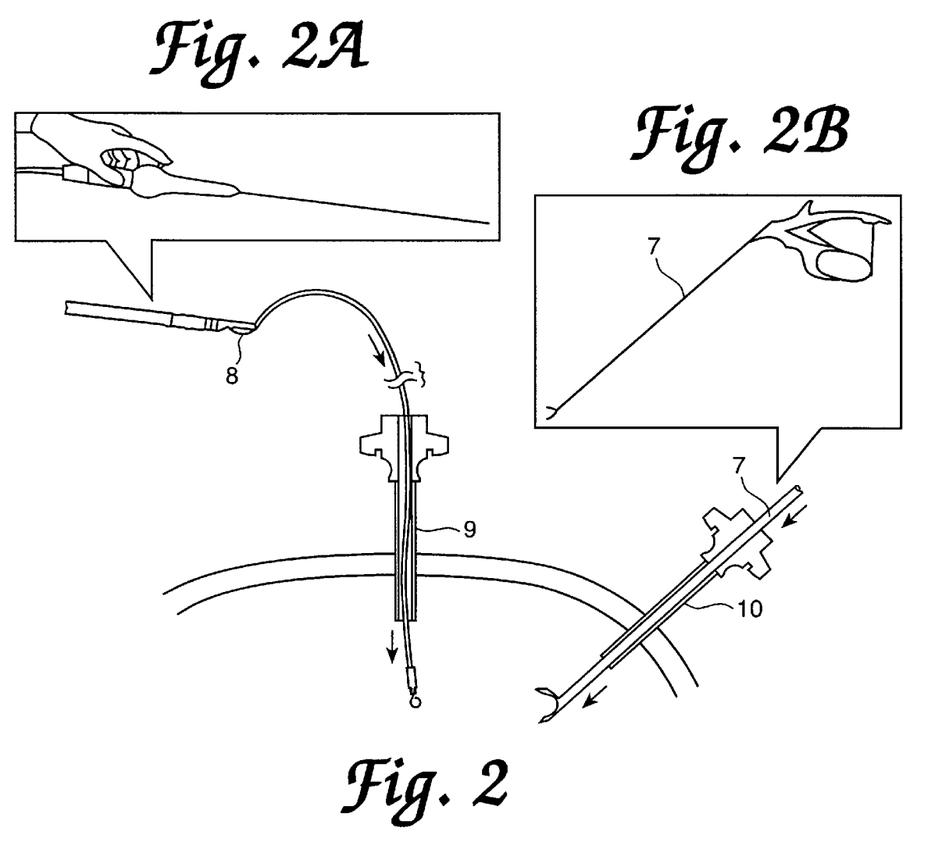
FIGS. 2, 2A and 2B illustrate how a needle guide and a surgical forceps can be inserted through their respective trocar.
Figures 3, 3A:
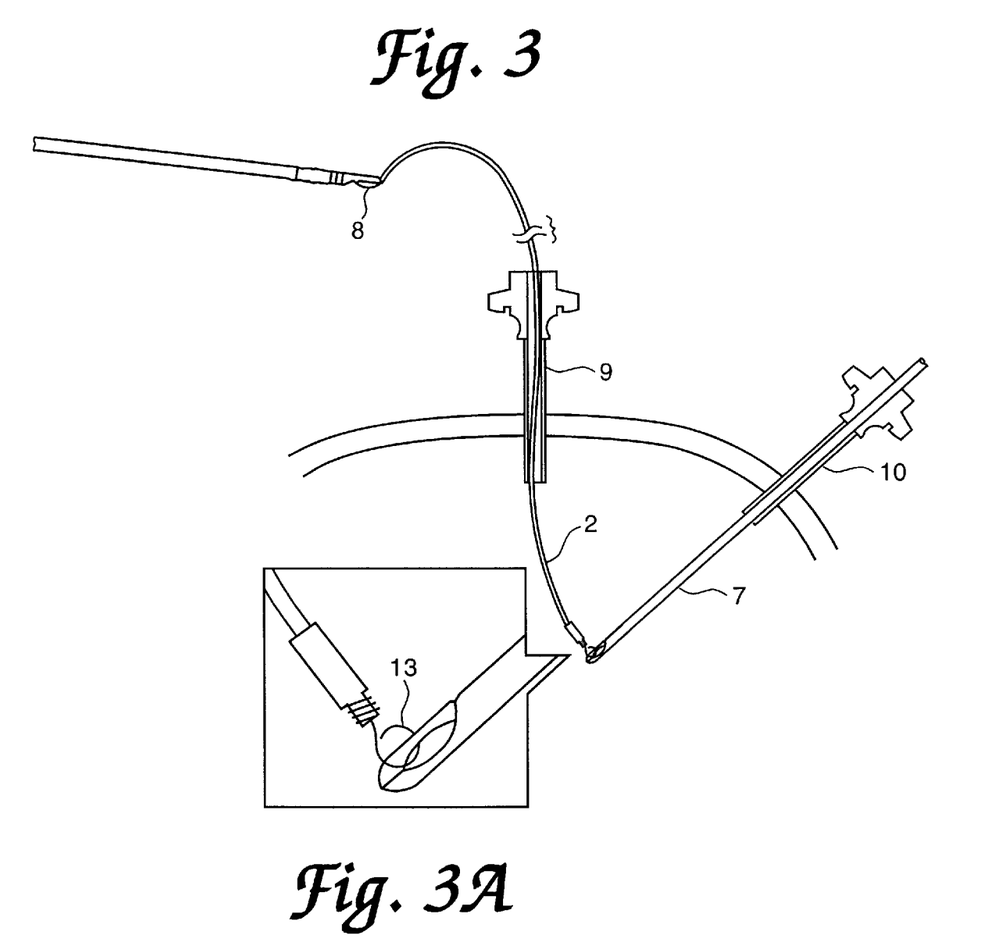
FIGS. 3 and 3A illustrate how the forceps can grip the end of the needle guide.
Figure 4:
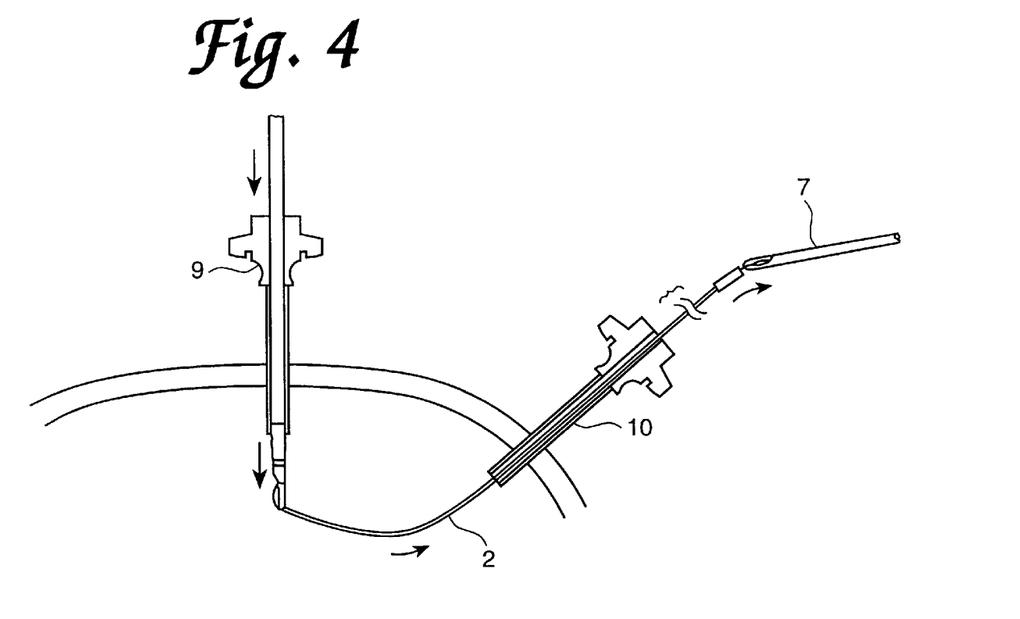
FIG. 4 illustrates how the needle guide can be retracted through one trocar by means of the forceps.
Figure 5:
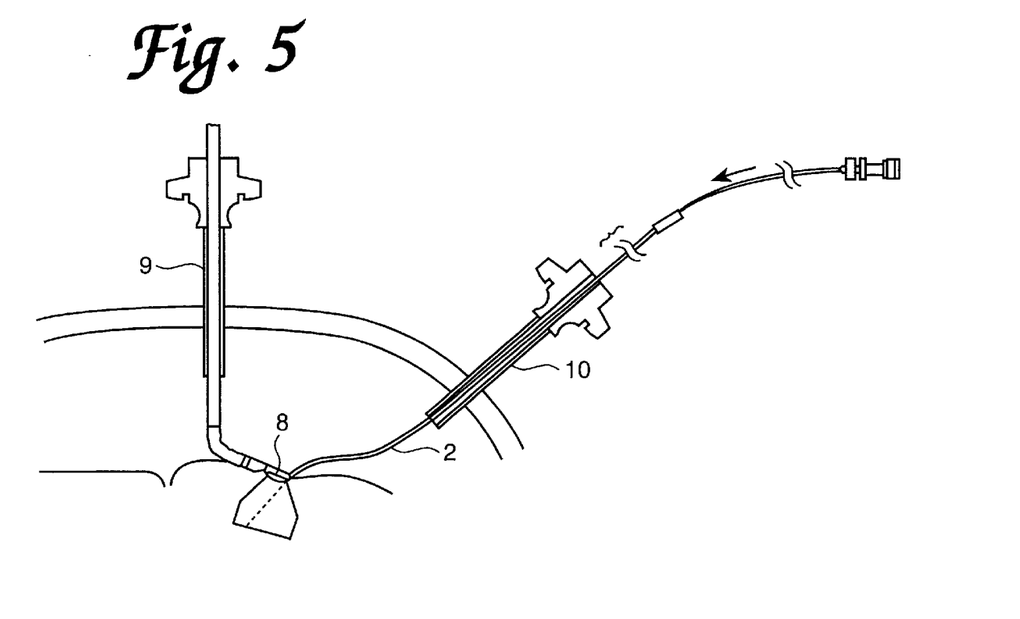
FIG. 5 illustrates how a needle can subsequently be inserted through the needle guide.

By the method according to the invention, a needle guide 2 is inserted in the abdominal cavity of a patient for the purpose of removing in an ultrasound-guided manner tissue samples (biopsies) from the patient through a trocar 9. The needle guide 2 comprises a mounting member for the mounting of the needle guide 2 on an ultrasonic transducer 8 at the end of a flexible catheter inserted through the same trocar 9, cf. FIG. 2. Initially, the distal end of the needle guide 2 is secured to the ultrasonic transducer 8 by means of the mounting member 1, the ultrasonic transducer being accommodated at the end of the catheter. Subsequently, the distal end of the needle guide 2 is inserted followed by insertion of the ultrasonic transducer 8 through the trocar 9. The distal end of the needle guide 2 is provided with a small eye, which can be caught by a pair of surgical forceps 7 inserted through a second trocar 10. Accordingly, the distal end of the needle guide 2 can be pulled upwards through the second trocar 10 by means of the forceps 7 at the same time as the ultrasonic transducer 8 is inserted through the first trocar 9. Now, the transducer 8 can be placed in the desired position, and a needle with a stiletto can be inserted through the needle guide 2. The trocars are, for instance, of the type described in European Patent Application No. 556,056. The catheter with the ultrasonic transducer can, for instance, be of the type B & K Medical type 8555 or of the type described in U.S. Pat. No. 4,605,009.

Such a method allows the operator to place the ultrasonic plane of the transducer and the needle guide 2 very accurately relative to the internal organs, and to perform ultrasound guided biopsies in arbitrary areas. The diameter of the needle is only limited by the trocar, through which the needle 3 is to be inserted. The flexibility of the needle 3 is of importance, but such flexibility is not as critical as previously.

In addition, this method allows a separation of the ultrasonic transducer and the needle guide, with the result that the cleaning of both the transducer 8 and the needle guide 2 has been facilitated. The needle guide system is made of metal and can therefore be subjected to a heat sterilization, in for instance an autoclave. Commercially available transducers are cleaned in sterilizing fluids at low temperatures.

Figure 6:
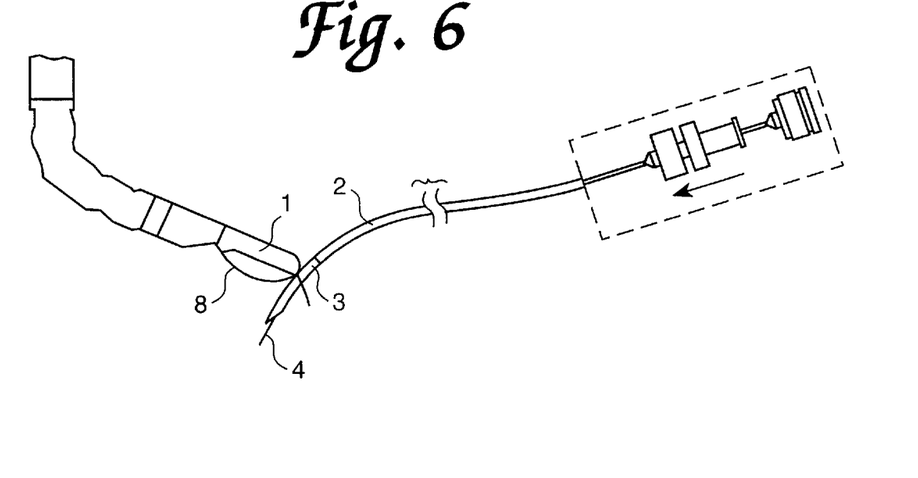
FIG. 6 illustrates how the needle is placed after the insertion.
Figure 7:
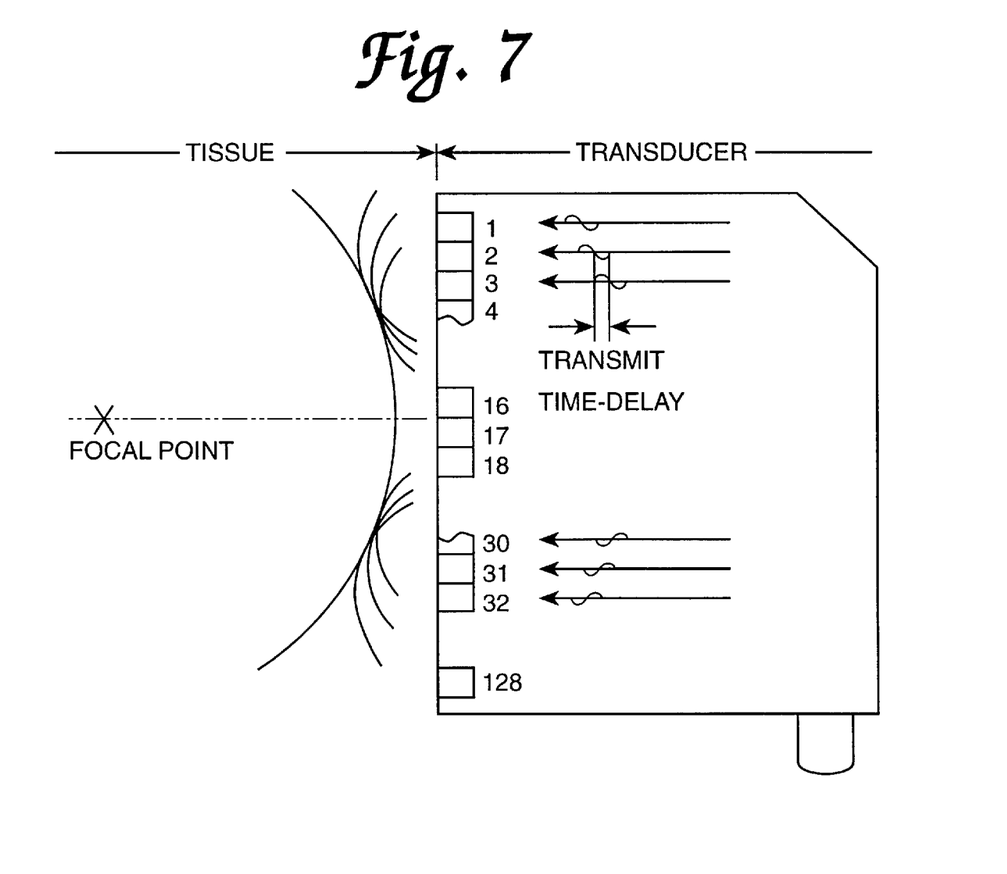
FIG. 7 is a detailed view of an embodiment of the ultrasonic transducer.

The needle guide 2 is mounted on the distal end of the transducer 8, cf. FIG. 6, and comprises a holder 1 or mounting member for the securing of the needle guide 2 to the transducer 8. The needle guide may be made of plastics, such as Teflon® polytetrafluoroethylene, which is not damaged by sharp needles, or as a bendable spiral made of stainless steel. At the end of the needle guide 2, where the holder 1 is mounted, the needle guide 2 has been made rigid either by way of securing to the holder 1 or by the needle guide 2 ending in a tube. In this manner, the needle guide 2 can guide the direction of the needle 3 despite the predominantly flexible character of the needle guide 2. A relatively long needle 3 with a stiletto 4 is inserted through the needle guide 2. The needle may be relatively thick. The needle 3 can, for instance, be of the type "fine" where it is optionally used together with a particular handle 5. The handle 5 allows an exact positioning of the needle 3. The needle 3 can also be of the type Tru-cut, optionally used together with an automatic biopsy apparatus 5 arranged for removing a tissue sample by way of suction.

The needle guide system according to the invention is relatively easy to use:

The distal end of the needle guide 2 is inserted through the trocar 9, through which the transducer 8 is also to be inserted. The distal end of the needle guide 2 is caught by a pair of forceps 7 inserted through a second trocar 10. The distal end of the needle guide 2 is then carried upwards through the second trocar 10 at the same time that the transducer 8 is inserted through the first trocar 9. The transducer 8 is then placed in the desired position, and the needle 3 can be inserted through the needle guide 2.

The ultrasonic transducer 8 is substantially of a circular shape and comprises a number of transducer elements activated in groups of, for instance, 5 or more juxtaposed elements, the signals to these elements being phase-shifted relative to one another in such a manner that the signals emitted are focused to a predetermined degree. The ultrasonic transducer 8 and the associated electronic circuits are, for instance, described in U.S. Pat. No. 4,605,009.

Figures 8A, 8B, 8C:
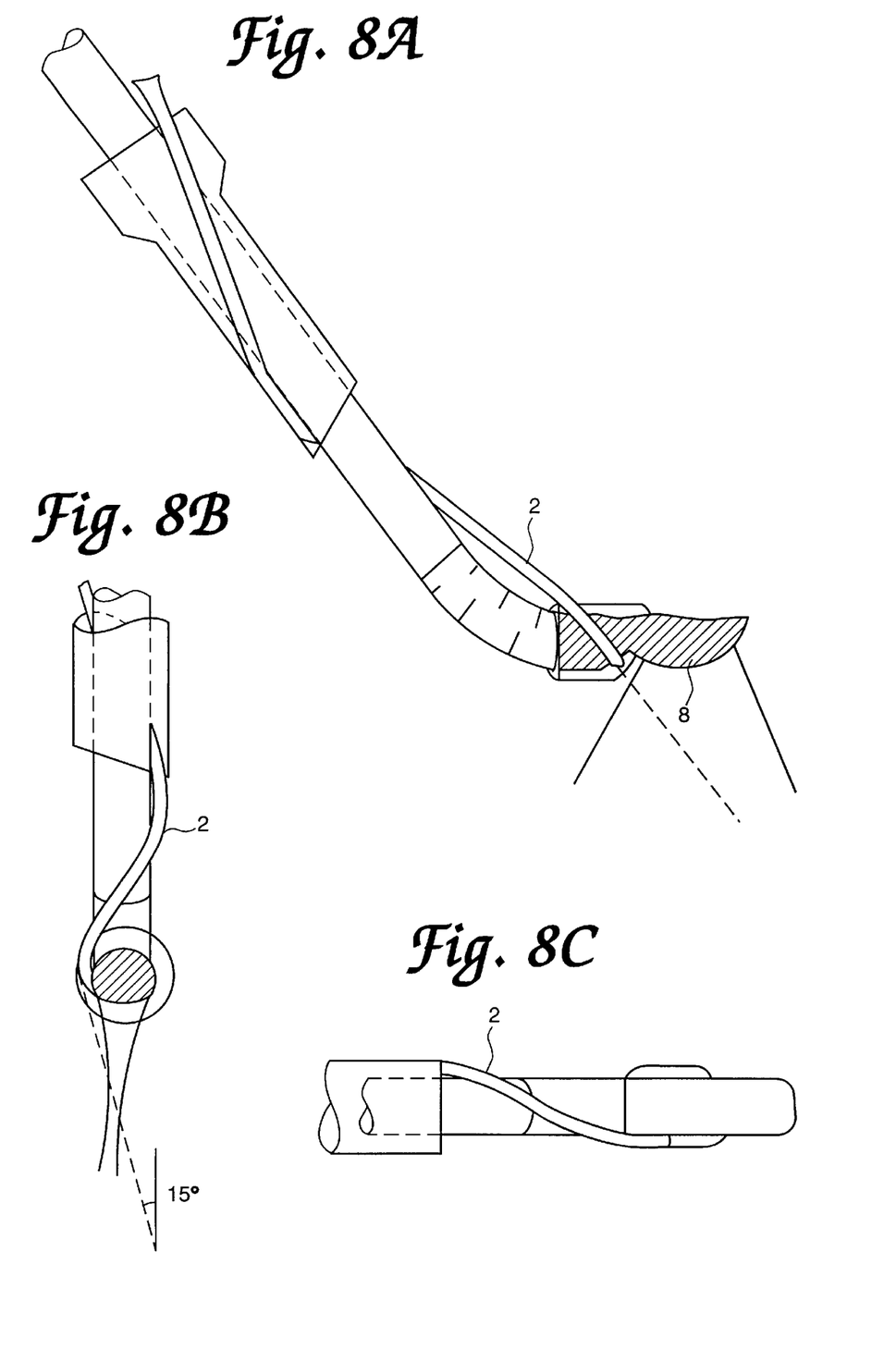
FIGS. 8A–8C illustrate an alternative positioning of the needle guide.
Figure 9A:
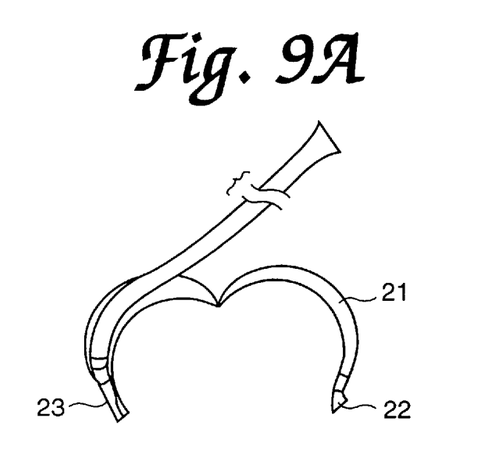
FIGS. 9A and 9B illustrate how the needle guide is secured to the catheter adjacent the ultrasonic transducer.
Figure 9B:
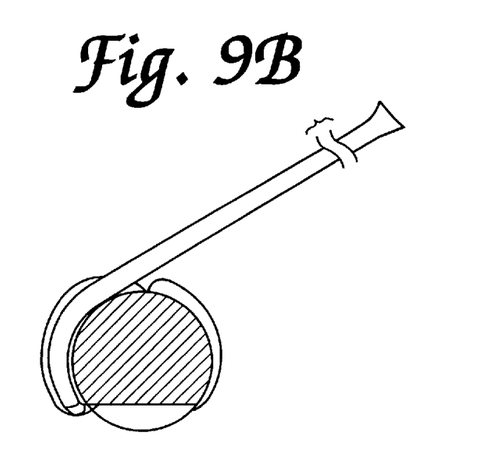
Figure 10:
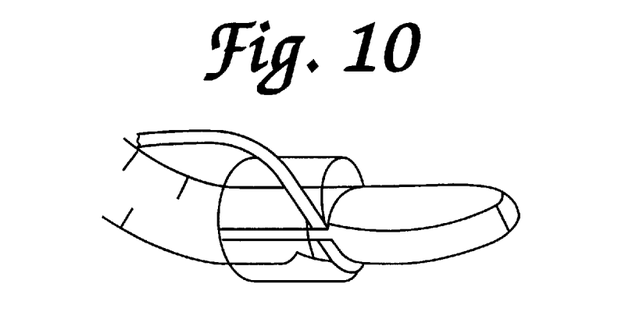
FIG. 10 illustrates the needle guide secured to the transducer.

The method illustrated in FIGS. 2 to 6 is, however, not applicable in case a biopsy is to be performed in the upper portion of the liver or the pancreas. In these cases, one lung obstructs one insertion. Therefore, the apparatus of FIG. 8 has been developed, this letter apparatus being based on the fact that the needle guide 2 is wound around the catheter for the ultrasonic transducer 8 and is inserted together with the transducer through one trocar. The mounting member 21 of the needle guide is clipped onto the catheter adjacent the transducer 8 in such a manner that the needle guide forms a permanent angle with the transducer. FIGS. 9A and 9B illustrate the clipping means 21 before and after the securing to the catheter. The clipping means 21 comprise the substantially circumferential members which can grip the catheter. These members are interconnected through a pivot joint, and the end of one member is shaped as a barb 22 and can be inserted in a correspondingly shaped opening 23 in the end of the other member. FIG. 10 is a perspective view of the clipping means 21 after the securing procedure. The permanent angle formed by the needle guide 2 and the transducer 8 can be utilized in connection with the display on a display unit associated therewith in such a manner that, in advance, it is possible to draw the rectilinear path of the needle on the display unit. As illustrated in FIGS. 8 to 10, the needle guide is arranged on the outside of the catheter. In theory, nothing prevents a user from drilling an opening in the catheter adjacent the transducer 8 so as to insert the needle guide 2 through the opening. The resulting needle guide is arranged at the center of the scanning field of the transducer 8. Such an opening is, however, difficult to clean and may expose the patient to a risk of infections. It has therefore been chosen to arrange the needle guide 2 on the side of the catheter, optionally in such a manner that it is placed in a groove or notch on the side of the transducer 8. Then, the needle guide 2 need only present an approximate angle in the transverse direction relative to the slightly blurred radiation field of the transducer. This angle is 5 to 45°, preferably 10 to 30°, especially 15°, cf. FIG. 8B. As a result, the needle is arranged inside a large portion of the scanned radiation field of the transducer 8. This field should be as narrow as possible in view of the resolution. It is, however, not possible to make this field extremely narrow, and it is thanks to the inventor that he has understood to utilize these incompletenesses.

When a notch is provided adjacent the transducer, the needle guide can, of course, be further inserted towards the center of the scanning field.

Figure 11:
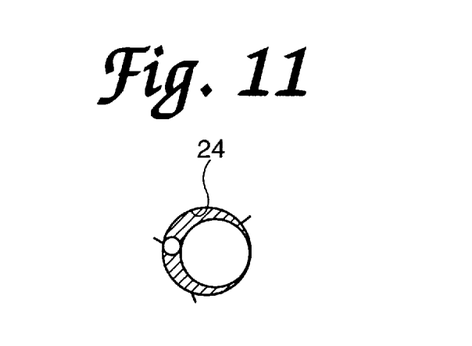
FIG. 11 illustrates how the needle guide is arranged in a groove of a circumferential jacket surrounding the catheter.

The needle guide can optionally be arranged in a groove of a jacket 24 surrounding the catheter, cf. FIG. 11, in such a manner that the needle guide does not cause leaks in connection with the combined insertion of the needle guide and the catheter through a trocar.

I claim:

1. Apparatus for providing ultrasound-guided removal of a tissue sample, comprising:

at least one trocar insertable in a wall defining a cavity of a subject, within which cavity a tissue exists from which the tissue sample is to be taken for removal;

an ultrasonic transducer arranged to be inserted through said at least one trocar into the body cavity;

a needle guide which is predominately flexible along the length thereof, but is rigid at one end;

a mounting member arranged for mounting the needle guide at said one end to said ultrasonic transducer such that the needle guide, at said one end thereof, forms a substantially permanent angle with said transducer;

said needle guide being arranged to have said one end thereof introduced into the body cavity through said at least one trocar, while having an opposite end extending out of the body cavity through said at least one trocar;

said needle guide being arranged to have a tissue sample-taking needle introduced through the needle guide and advanced through said one end into the tissue from which the tissue sample is to be taken for removal, while the ultrasonic transducer is located in the body cavity; and a display arranged to be associated with the ultrasonic transducer while the ultrasonic transducer is located in the body cavity, for enabling a user to guide the one end of the needle in an image plane of said ultrasonic transducer, while observing imaging of the one end of the needle on said display.

2. The apparatus of claim 1, further including:

said ultrasonic transducer being supported at one end of a catheter which is arranged to extend from the ultrasonic transducer, and out of the body cavity through said at least one trocar as the ultrasonic transducer is introduced into the body cavity through said at least one trocar.

3. The apparatus of claim 2, further including:

said needle guide, adjacent said one end, being wound around said catheter, for facilitating introduction of said one end of said needle guide and said ultrasonic transducer into the body cavity through a same trocar of said at least one trocar.

4. The apparatus of claim 1, wherein:

said substantially permanent angle is 30° to 60°.

5. The apparatus of claim 1, wherein:

in a transverse direction, said needle guide, at said one end thereof, forms an angle of 5° to 30° with said image plane of said ultrasonic transducer.

6. The apparatus of claim 1, wherein:

said mounting member comprises a groove provided in said ultrasonic transducer and arranged for having said one end of said needle guide received therein.

7. The apparatus of claim 1 wherein:

said groove extends at an angle 30° to 60° to the lengthwise direction of the ultrasonic transducer.

8. A method for obtaining a tissue sample from a tissue located within a cavity of a subject, comprising the steps of:

inserting at least one trocar in a wall of the subject, so as to provide access to the cavity;

inserting an ultrasonic transducer through said at least one trocar into the body cavity;

providing a needle guide which is predominately flexible along the length thereof, but is rigid at one end;

mounting the needle guide by a mounting member at said one end to said ultrasonic transducer such that the needle guide, at said one end thereof, forms a substantially permanent angle with said transducer;

introducing said one end of said needle guide into the body cavity through said at least one trocar, while having an opposite end extending out of the body cavity through said at least one trocar;

through use of a display associated with the ultrasonic transducer while the ultrasonic transducer is located in the body cavity, a user guiding the one end of the needle guide in an image plane of said ultrasonic transducer, while observing imaging of the one end of the needle guide on said display; and introducing a tissue sample-taking needle introduced through the needle guide and advancing said needle through said one end into the tissue from which the tissue sample is to be taken for removal, while the ultrasonic transducer is located in the body cavity, and taking the tissue sample from the tissue via the needle.

* * * * *